(12) United States Patent
Burg et al.

(10) Patent No.: US 6,399,333 B1
(45) Date of Patent: Jun. 4, 2002

(54) PROCESS FOR PRODUCING ERYTHROPOIETIN CONTAINING NO ANIMAL PROTEINS

(75) Inventors: Josef Burg; Walter Schneider, both of Weilheim; Alexander Wrba; Werner Fürst, both of Penzberg; Karl-Heinz Sellinger, Weilheim, all of (DE)

(73) Assignee: Roche Diagnostics GmbH, Mannheim (DE)

( * ) Notice: Subject to any disclaimer, the term of this patent is extended or adjusted under 35 U.S.C. 154(b) by 0 days.

(21) Appl. No.: 08/945,802

(22) PCT Filed: May 10, 1996

(86) PCT No.: PCT/EP96/01988

§ 371 (c)(1),
(2), (4) Date: Feb. 13, 1998

(87) PCT Pub. No.: WO96/35718

PCT Pub. Date: Nov. 14, 1996

(30) Foreign Application Priority Data

May 11, 1995 (EP) .............................. 95107165
Jun. 21, 1995 (DE) .......................... 195 22 461

(51) Int. Cl.⁷ .......................... C12P 21/04; C12P 21/06; C12N 1/20; C07H 21/04
(52) U.S. Cl. .................. 435/69.6; 435/69.1; 435/252.3; 435/320.1; 435/325; 435/404; 514/2; 514/12; 514/814; 536/23.1
(58) Field of Search .............................. 435/69.1, 69.6, 435/325, 404, 252.3, 320.1; 514/2, 12, 814; 536/23.1

(56) References Cited

U.S. PATENT DOCUMENTS 4,954,437 A * 9/1990 Beck ........................ 435/69.4

FOREIGN PATENT DOCUMENTS

| EP | 0 267 678 | 5/1988 |
| EP | 0 358 463 | 3/1990 |
| EP | 0 513 738 | 5/1992 |

OTHER PUBLICATIONS

Navhi, L.O. et al. *J. Biol. Chem.* 266:23022–23026 (1991).*
Nobuo Imai et al., 6038 *The Journal of Biochemistry* 107(1990) Mar., No. 3, "Physicochemical and Biological Comparison of Recombinant Human Erythropoietin with Human Urinary Erythropoietin".
International Publication No. WO 86/07594, published Dec. 31, 1986.
Jeannie Choppin et al., *Exp. Hematol.*, 15:171–176 (1987), "Biochemical Analyses of Murine Erythropoietin from Plasma and from Cloned Erythroleukemia Cells".
International Publication No. WO 86/04068, published Jul. 17, 1986.
International Publication No. WO 85/02610, published Jun. 20, 1985.
Kenneth Jacobs et al., *Nature*, vol. 313, Feb. 28, 1985 "Isolation and Characterization of Genomic and cDNA Clones of Human Erythropoietin".
Budesverband der Pharmazeutischen Industrie BV.: "Rote Liste 1993".
Gerald Krystal et al., *The Journal of The American Society of Hematology*, vol. 67, No. 1, Jan. 1986, Purification of Human Erythropoietin to Hemogenetity by a Rapid Five–Step Procedure.
Robert M. Kennedy, *Methods in Enzymology*, vol. 182, "Hydrophobic Chromatography"(1990).

* cited by examiner

Primary Examiner—Tekchand Saidha
(74) Attorney, Agent, or Firm—Arent Fox Kintner Plotkin & Kahn, PLLC.

(57) ABSTRACT

A process for producing erythropoietin which is free of foreign animal proteins except for the proteins of the host cell, wherein DNA coding for EPO is expressed in a eukaryotic host cell and the host cell is cultured in a medium free of natural mammalian proteins. The erythropoietin is chromatographically purified using dye affinity chromatography, chromatography on hydroxyapatite, reversed phase chromatography, and anion exchange chromatography. The resulting preparation contains less than 100 ppm of proteins derived from the host cell, and less than 10 pg of host cell DNA per 83 μg erythropoietin.

9 Claims, No Drawings

PROCESS FOR PRODUCING ERYTHROPOIETIN CONTAINING NO ANIMAL PROTEINS

The invention concerns a process for producing erythropoietin which is free of animal foreign proteins with the exception of proteins of the host cell. Erythropoietin (EPO) is a human glycoprotein which stimulates the formation of erythrocytes. Its action and therapeutic application are described in detail for example in EP-B 0 148 605, Huang, S. L., Proc. Natl. Acad. Sci. USA (1984) 2708–2712, EP-B 0 205 564, EP-B 0 209 539 and EP-B 0 411 678 as well as Lai, P.H. et al., J. Biol. Chem. 261 (1986) 3116–3121 and Sasaki, H. et al., J. Biol. Chem. 262 (1987) 12059–12076. Erythropoietin for therapeutic use is produced by recombinant means (EP-B 0 148 605 and EP-B 0 209 539).

The recombinant production of erythropoietin is usually carried out in CHO cells with the addition of foetal calf serum and optionally bovine insulin in the culture medium. As a result an EPO preparation produced in this manner contains at least traces of substances which are derived from these additives even after purification.

These may for example be bovine viruses and comparable agents, residual amounts of bovine proteins and/or bovine DNA.

It is known that a serum-free fermentation of recombinant CHO cells which contain an EPO gene can be carried out using the methods of the state of the art.

Such methods are described for example in EP-A 0 513 738, EP-A 0 267 678 and in a general form by Kawamoto, T. et al., Analytical Biochem. 130 (1983) 445–453, EP-A 0 248 656, Kowar, J. and Franek, F., Methods in Enzymology 421 (1986) 277–292, Bavister, B., Expcology 271 (1981) 45–51, EP-A 0 481 791, EP-A 0 307 247, EP-A 0 343 635, WO 88/00967. It has turned out that in a serum-free culture of EPO-producing eukaryotic host cells the proportion of proteins of the host cell relative to the total protein amount is more than twice that of a culture in media containing serum. Such a protein preparation also contains nucleic acids from the host cells in a not inconsiderable amount.

In EP-A 0 267 678 an ion exchange chromatography on S-Sepharose, a preparative reverse phase HPLC on a $C_8$ column and a gel filtration chromatography are described for the purification of EPO produced in serum-free culture after dialysis. In this connection the gel filtration chromatography step can be replaced by ion exchange chromatography on S-Sepharose fast flow. It is also proposed that a dye chromatography on a Blue Trisacryl column be carried out before the ion exchange chromatography.

EPO purified in this manner has a purity of about 99% but still contains considerable amounts of protein and DNA from the host cell.

A process for the production of EPO in mammalian cells is described in EP-A 0 513 738 without elaborating on the purification.

A process for the purification of recombinant EPO is described by Nobuo, I. et al., J. Biochem. 107 (1990) 352–359. In this process EPO is treated however with a solution of Tween® 20, phenylmethylsulfonyl fluoride, ethylmaleimide, pepstatin A, copper sulfate and oxarnic acid prior to the purification steps. Although the pharmaceutical preparation contains only traces of these additives they are critical from the therapeutic point of view.

Moreover, for a therapeutic use it is preferred that a therapeutically effective preparation should be completely free of proteins and nucleic acids from mammalian cells and largely free of proteins and nucleic acids from the host cell.

The subject matter of the invention is a therapeutically effective preparation of a protein with erythropoietin activity obtainable after culturing a host cell which produces erythropoietin characterized by:

a) a content of proteins which are derived from the host cell of not more than 100 ppm (w/w), preferably 40 ppm or less, and more preferably 20 ppm or less, b) a content of DNA from the host cell of not more than 10 pg per 83 μg EPO, preferably 1 pg per 83 μg EPO or less, and in that c) the preparation is completely free of natural mammalian proteins which are not derived from the host cell.

Such an EPO preparation which in addition is free of phenylmethylsulfonyl fluoride, pepstatin A and/or Cu ions is previously unknown and also cannot be produced by the methods of the state of the art especially in therapeutically effective amounts. In order to obtain and to isolate a homogeneous EPO preparation of this specification, it is necessary to combine the steps of the process according to the invention.

A protein with erythropoietin activity is understood as a protein which has the biological function of EPO. This biological function is to stimulate differentiation and division processes in erythroid precursor cells and thus to provide erythrocytes. The properties of this protein are preferably identical to or essentially identical to those of human erythropoietin and it is composed of 166 amino acids with a molecular weight of ca. 34–38 kD the percentage of glycosyl residues in the molecular weight being ca. 40%. Derivatives and fragments of EPO which have an analogous activity and are produced after culturing an EPO-producing host cell, can also be produced in a pure form by the processes according to the invention. The DNA and protein sequences of human EPO are described for example in EP-B 0 205 564 and EP-B 0 209 539.

"Completely free of natural mammalian proteins" means that due to the fact that no foreign proteins from natural sources such as bovine serum albumin or foetal calf serum are added during the culture of the host cell, no such foreign proteins are present to a detectable extent in the preparation. The preparation is thus completely free of such mammalian proteins added as planned that are not derived from the host cell and are usually added to the culture medium in a serum-free culture to maintain and improve cell growth and to optimize the yield. Natural mammalian proteins are understood as mammalian proteins from natural sources such as from human material or from animal material but not recombinant mammalian proteins which are for example produced in prokaryotes such as E. coli.

Such mammalian proteins added during cell culture are for example bovine serum albumin, foetal calf serum, transferrin (human or bovine), insulin (porcine or bovine) or gelatin.

A "host cell" is understood as an animal or human cell whose genome contains an active EPO gene and this EPO gene is transcribed and translated during culture of the cell in a serum-free medium. The EPO gene can be introduced into this host cell as an exogenous gene, preferably with regulation elements (cf. e.g. EP-B 0 148 605, EP-B 0 209 539), already be present in the host cell as an active endogenous gene or become activated as an endogenous non-active gene. Such an activation of endogenous genes can for example be achieved by the specific introduction of regulation elements into the genome for example by homologous recombination. Such methods are known and are described for example in WO 91/09955.

Mammalian cells are usually used as host cells. If an exogenous human EPO gene is introduced, CHO or BHK cells can for example be used as host cells. If an endogenous EPO gene is used for the expression, it is expedient to use human cells such as for example kidney, liver or lymph cells.

"Proteins which are derived from the host cell" are understood as proteins which are formed during the culture of the host cells containing the active EPO gene and do not have the specifications of EPO described above. The protein content is stated in ppm relative to weight (w/w). The content of these proteins can for example be determined by an ELISA which is based on polyclonal antibodies that are directed against the proteins of the host cell. Such polyclonal antibodies are obtained by immunizing animals, preferably sheep, with an extract of the proteins of the host cell (extracellular and intracellular proteins). The test is preferably carried out as a sandwich test using an immobilized polygonal antibody and a peroxidase-labelled second antibody. The total protein extract is used as a standard. The lower limit of detection of such a test is about 15 ng protein per ml. At a common EPO concentration of about 3.0 mg/ml this corresponds to an amount of 5 ppm proteins from the host cell as the lowest detectable amount. Thus the preparation according to the invention preferably contains proteins from the host cell in an amount of 5 ppm to 100 ppm. An EPO preparation is particularly preferably used in which proteins from the host cell are no longer detectable in this manner.

"DNA from the host cell" is to be understood as the total amount of DNA of this host cell (genomic, ribosomal, mitochondrial etc. DNA). This content also includes the DNA which codes for EPO and which was for example obtained by transformation with an exogenous DNA. It is expedient to relate this to the therapeutic dose of EPO which is usually used of 83 $\mu$g. The content of DNA of the host cell is determined by a hybridization test using radioactive or fluorescent detection. The total DNA from the host cell is used as the probe DNA. This total DNA is used as a standard in this test. The lower limit of detection of such a hybridization test is about 1 pg DNA/83 $\mu$g EPO. The preparation according to the invention preferably contains DNA from the host cell in an amount of 1–10 pg, or more preferably less than 5 pg per 83 $\mu$g EPO. It is most preferred that DNA can no longer be detected in the preparation in this manner ($\leq$1 pg DNA).

The invention in addition concerns a process for the production of a protein preparation with human erythropoietin activity which is characterized by:

a) a content of proteins which are derived from the host cell of not more than 100 ppm (w/w), preferably 40 ppm or less, and more preferably 20 ppm or less, b) a content of DNA from the host cell of not more than 10 pg per 83 $\mu$g EPO, preferably 1 pg per 83 $\mu$pg EPO or less, and in that c) the preparation is completely free of natural mammalian proteins which are not derived from the host cell by expressing a DNA coding for EPO in a eukaryotic host cell, culturing the host cell in a medium free of natural mammalian proteins, chromatographically purifying EPO from the cell supernatant by dye affinity chromatography, chromatography on hydroxyapatite, reversed phase chromatography and anion exchange chromatography, wherein a hydrophobic chromatography on a butylated support is carried out after the dye affinity chromatography.

Surprisingly it has been found that with this process EPO having a high purity can be obtained in high yields preferably from a serum-free culture. In comparison with the process described by Nobuo, I. et al., J. Biochem. 107 (1990) 352–359, for instance, a yield increased by approximately a factor of 2 (25% as compared to 13% in Nobuo et al.) is obtained in a competitive ELISA assay for EPO.

The competitive ELISA assay used for detecting EPO was carried out with the following steps: Coating a microtiter plate with a polyclonal antibody directed against mouse Fc$\gamma$; reaction with a monoclonal antibody against EPO from mouse; competition between EPO sample and peroxidase-labelled EPO; substrate reaction with ABTS® (2,2'-acino-di-e(3-)ethylbenzthiazoline sulfonate(6)].

The protein preparation is preferably produced in batches of 0.1–10 g. It has surprisingly turned out that an adequate purification of EPO for therapeutic applications can only be achieved after culture in a medium which is free of natural mammalian proteins if, after the affinity chromatography on a dye, a hydrophobic chromatography is carried out as a second step. It is surprisingly not necessary to add protease inhibitors (e.g. CuSO$_4$) prior to the chromatographic purification as described by Nobuo, I. et al., J. Biochem. 107 (1990) 352–359 or in WO 86/07494. The hydrophobic chromatography is preferably carried out on an alkylated ($C_4$–$C_{18}$) or arylated (preferably phenylated or benzylated) support. A butylated support is particularly preferably used. In this case the yield of the purification process and the purity of the protein are particularly high.

Expression of a DNA coding for EPO in a eukaryotic host cell can for example be carried out by transfecting a suitable host cell, preferably CHO cells, with an exogenous DNA which codes for EPO. It is also possible to activate an endogenous EPO gene which is inactive in the cell (for example human kidney cells) for example by a homologous recombination method (WO 91/09955 and WO 93/09222). The culture of host cells containing an active EPO gene is carried out in a manner known to a person skilled in the art in a culture to which no mammalian proteins from natural sources are added. However, insulins, albumins and transferrins produced recombinantly (preferably in prokaryotes, such as E. coli) are usually added during this culture.

A serum-free medium which is suitable within the scope of the invention for example contains as the medium DMEM/F12 (e.g. GRH Biosciences/Hazleton Biologics, Denver, US, order No. 57-736) and additionally sodium hydrogencarbonate, L+glutamine, D+glucose, recombinant insulin, sodium selenite, diaminobutane, hydrocortisone, iron(II) sulfate, asparagine, aspartic acid, serine and a stabilizer for mammalian cells such as e.g. polyvinyl alcohol, methyl cellulose, polydextran, polyethylene glycol, Pluronic F68, plasma expander polygelin (HEMACCEL) or polyvinyl pyrolithione.

It is an essential advantage of the process for the purification of EPO according to the invention that with this process one succeeds in purifying EPO in a high yield, which after culturing free of serum, contains one of the above-mentioned stabilizers, and in removing the stabilizer/stabilizers to such an extent that it is/they are no longer detectable.

In order to produce EPO the host cell containing the EPO gene is adapted to the medium which contains no mammalian proteins from natural sources by passaging in low-volume cultures. The adapted cells are optionally kryopreserved, taken as required from the cell bank and expanded in serum-free medium.

For purification the cell-free culture supernatant of the host cell is preferably isolated and subjected to the purification process according to the invention after filtration.

Before carrying out the purification process it is possible to carry out an additional filtration if necessary to separate turbidities and/or a concentration.

In the first step the dye chromatography mainly removes contamination by proteases. A blue triazine dye such as Cibachron® blue is preferably used as the dye. Other triazine dyes are also suitable. The support material for the dye chromatography is not critical, however, a support material based on polysaccharides is preferably used such as e.g. sepharose, preferably Sepharose 6 fast flow. The column is equilibrated with buffer, pH 4.5–5.5, preferably 4.8–5.2, preferably with acetate buffer or acetic acid. Preferably temperatures of 1–10° C., more preferably of about 5° C. are applied.

The elution can be achieved by increasing the salt concentration at an acidic or neutral pH value (preferably pH 5–7). At a basic pH value, preferably pH 8.5–9.5, particularly preferably at pH 8.8–9.2, the elution can also be carried out without a significant change in the salt concentration.

An important factor for the quality of the purification is that a chromatography on a hydrophobized support is carried out in the second step. Suitable adsorber materials for hydrophobic chromatography are described for example in Protein Purification Methods, A practical approach, Ed. Harris, E. L. V. and Angal. S., IRL Press Oxford, England (1989) p. 224 and Protein Purification, Ed. Janson, J. C., Ryden L, VCH-Verlag, Weinheim, Germany (1989) pp. 207–226. The support material itself is not critical and can for example be Sepharose, a copolymer of acrylic acid and methacrylic acid or silica gel. It is important that hydrophobic groups, preferably butyl groups, are covalently bound to this support. Suitable supports are commercially available (e.g. butyl-Toyopearl from Toso Haas, Germany or butylsepharose from Pharmacia, Germany).

A butylated support is particularly preferably used. other alkylated or arylated supports either partially bind EPO irreversibly or lead to a poorer separation.

Elution in the hydrophobic chromatography is preferably achieved by lowering the salt concentration (e.g. with a gradient of 4 mol/l to 0 mol/l or by addition of chaotropic agents such as iodide, perchlorate or thiocyanate or by addition of alcohols such as glycerol, ethylene glycol or isopropanol.

The hydrophobic chromatography is particularly preferably carried out at a neutral pH value and in the presence of salt, preferably NaCl ca. 0.75 mol/l. It is also particularly preferred that the hydrophobic chromatography be preferably carried out in the presence of a lower molecular alcohol and particularly preferably in the presence of isopropanol. The concentration of the alcohol in the elution buffer is preferably about twice to three times as high as in the equilibration buffer, and in the washing buffer about twice as high as in the equilibration buffer. Preferaby, approximately 10–15%, preferably about 10% isopropanol is added for equilibration (loading of the chromatographic material) for the elution about 25% to 35%, preferably about 27% isopropanol is added and 19% isopropanol is added in the washing buffer (the concentrations are also suitable for other alcohols, stated in volume%, v/v).

The hydrophobic chromatography can be carried out within a wide temperature range of ca. 10–40° C. However, it is preferable to use a controlled temperature at 27±2° C. Temperatures below 10° C. are less suitable.

A separation on hydroxyapatite is carried out as a further purification step in the process according to the invention. It is expedient that the column material is composed of hydroxyapatite which is embedded in an agarose matrix. EPO binds to this matrix and is preferably eluted at low phosphate concentrations. A suitable column material is for example hydroxyapatite-Ultrogel (Biosepra, Germany) or HA-Biogel HT (Biorad, Germany).

It is expedient to carry out the chromatography at an approximately neutral pH value. The elution buffer contains phosphate, preferably potassium phosphate at a concentration of 1 mmol/l to 100 mmol/l, preferably ca. 10 mmol/l.

This is followed by a reversed phase chromatography on a hydrophobized support as a further step in the purification. This is preferably the support which is also used for the hydrophobic chromatography. Materials which are for example suitable as chromatography materials for the reversed phase chromatography are: phenylsepharose and octylsepharose (Pharmacia, Sweden), butyl-Toyopearl (Toso Haas, Germany) or propyl-TSK (Merck, Germany). However, it is also preferable in this process step to use supports which contain longer alkyl groups (e.g. $C_8$ or $C_{18}$). The column is preferably equilibrated in a pH range between 2 and 7, preferably pH 2.5 in which aqueous trifluoroacetic acid is preferably used. A gradient from the equilibration buffer to an aqueous solution of a polar organic solvent such as for example acetonitrile is used for the elution. It is expedient to neutralize the eluate after the chromatography.

An anion exchange chromatography follows as the next step of the purification process according to the invention. In this case DEAE-Sepharose fast flow is preferably used as the column material. The equilibration is carried out at pH 6–9, preferably at pH 7.5. Optionally after washing, preferably with an acidic solution (ca. pH 4.5), it is eluted in a neutral or slightly basic range (pH 6–9, preferably at pH 7.5 while increasing the ionic strength, preferably with NaCl). Phosphate buffer is preferably used as the buffer.

The following examples further illustrate the process according to the invention:

EXAMPLE

1. Starting Material

EPO is fermented in CHO cells by a batch process.

The fermenter is inoculated with a preculture and the fermenter contents are harvested after ca. 5 days. After harvesting the CHO cells are removed from the fermentation broth by centrifugation. The cell-free culture supernatant is adjusted to pH 5.0–5.2 with 1 mol/l acetic acid and filtered at 1–9° C.

A serum-free medium is used as the culture medium which is composed of the basic medium DME(HG) HAM's F-12 modified (R5) (GRH Biosciences/Hazleton Biologics, Denver, USA, Order No. 57-736), sodium hydrogencarbonate, L-(+) glutamine, D-(+) glucose, recombinant insulin, sodium selenite, diaminobutane, hydrocortisone, ironil sulfate, asparagine, aspartic acid, serine and polyvinyl alcohol.

2. Blue-Sepharose Chromatography 2.1 Separation Principle

Blue Sepharose (Pharmacia) is composed of Sepharose beads on the surface of which the dye Cibacron® blue is covalently bound. EPO binds to this support at a low ionic strength and neutral to acidic pH values. EPO is eluted by increasing the ionic strength and the pH value.

2.2 Procedure

The chromatography column (Amicon P440×500, Amicon, GB) is filled with 60–80 l blue Sepharose and regenerated with 0.5 N NaOH. The column is subsequently equilibrated with ca. 3 column volumes (CV) of acetate buffer. The cell-free culture supernatant adjusted to pH 5 is applied to the column at a temperature of 10±5° C. and at a flow rate of 800–1400 ml/min. The column is rewashed at the same flow rate and 5±4° C. with ca. 1 CV washing buffer 1. This is then followed by ca. 2 CV washing buffer 2. Subsequently the column is eluted with ca. 3 CV elution buffer. The total protein peak is collected (ca. 30–60 l), adjusted with HCl to pH 6.9 and stored at 5±4° C. until further processing. At this chromatographic step the product solution is concentrated and a purity of ca. 40–50% is achieved.

Equilibration buffer: 20 nM Na acetate, 5 mM $CaCl_2$, 0.1 M NaCl, pH 5.0±0.2

Washing buffer 1: 20 mM Na acetate, 5 mM $CaCl_2$, 0.25 M NaCl, pH 5.0±0.2

Washing buffer 2: 20 mM Tris HCl, 5 mM $CaCl_2$, pH 6.5±0.3

Elution buffer: 100 mM Tris HCl, 5 mM $CaCl_2$, 1 M NaCl, pH 9.0±0.2.

3. Butyl-Toyopearl Chromatography (Hydrophobic Chromatography)

3.1 Separation Principle

Butyl-Toyopearl (TosoHaas) is a support on whose surface butyl residues are covalently bound. EPO binds to this matrix and is eluted with a buffer containing isopropanol.

3.2 Loading and Elution Conditions

After binding the protein to the butyl matrix in an equilibration buffer which contained 10% isopropanol, the EPO was eluted by a gradient composed of aqueous buffer solution and 50% isopropanol. This elution begins above ca. 20% isopropanol.

It was expected that the addition of the elution agent isopropanol in the equilibration buffer would minimize the binding of "foreign proteins" and weaken the binding of EPO (lower capacity). surprisingly it was found that the addition of isopropanol in the equilibration buffer at defined concentrations (10–15%) increases the binding of EPO and thus also improves the yield (cf. Table 1).

EPO does not bind to butyl-Toyopearl at +4° C. At +25° C. 800 μg EPO/ml adsorber is bound (increased to 1000 μg/ml by isopropanol) and at +35° C. surprisingly in fact 1700 μg EPO/ml butyl-Toyopearl is bound.

TABLE 1

Dependency of EPO adsorption and desorption on the addition of isopropanol

| % isopropanol in the equilibration buffer | 0 | 10 | 15 | 17 | 19 |
|---|---|---|---|---|---|
| % EPO in the washing buffer | 24 | <1 | <1 | <1 | 10 |
| % EPO in the eluate | 76 | 96 | 93 | 83 | 69 |

3.3 Procedure

The chromatography column (Pharmacia BPG 300/500) is filled with 30–40 l butyl-Toyopearl and regenerated with 4 M guanidine-HCl and 0.5 N NaOH. The column is subsequently equilibrated with at least 3 CV equilibration buffer. The eluate of the blue Sepharose column is adjusted to 10% isopropanol and applied to the column at a temperature of 27±2° C. and a flow rate of 800–1200 ml/min. The column is rewashed at the same temperature and flow rate with ca. 1 CV equilibration buffer and then with ca. 2 CV washing buffer. Subsequently it is eluted with ca. 3 CV elution buffer. The total protein peak is collected (ca. 10–18 l), immediately diluted by a factor of 3 with the dilution buffer and stored at 15° C. until further processing. A purity of ca. 90% is achieved in this chromatography.

Equilibration buffer: 20 mM Tris-HCl, 5 mM $CaCl_2$, 0.75 M NaCl, 10% isopropanol, pH 6.9+0.2

Washing buffer: 20 mM Tris-HCl, 5 mM $CaCl_2$, 0.75 M NaCl, 19% isopropanol pH 6.9±0.2

Elution buffer: 20 mM Tris-HCl, 5 mM $CaCl_2$, 0.75 M NaCl, 27% isopropanol pH 6.9±0.2

Dilution buffer: 20 mM Tris-HCl, 5 mM $CaCl_2$, pH 6.9±0.2

4. Hydroxyapatite Ultrogel Chromatography 4.1 Separation Principle

Hydroxyapatite Ultrogel (Biosepra) is composed of hydroxyapatite (crystalline calcium phosphate) which is embedded in an agarose matrix in order to improve its mechanical and hydrodynamic properties. EPO binds to this matrix and is eluted at a lower phosphate concentration than most of the protein impurities.

4.2 Procedure

The chromatography column (Amicon P440×500 or equivalent) is packed with 30–40 l hydroxyapatite Ultrogel and regenerated with 0.5 N NaOH. The column is subsequently equilibrated with at least 4 CV equilibration buffer.

The eluate of the butyl-Toyopearl column is applied to the column at a temperature of ca. 15° C. and a flow rate of 500–1200 ml/min. The column is rewashed at the same temperature and flow rate with ca. 1 CV equilibration buffer and then with ca. 2 CV washing buffer. Subsequently it is eluted with ca. 3 CV elution buffer. The total protein peak is collected (ca. 10–18 l) and stored at 15° C. until further processing. A purity of more than 95% is achieved in this chromatography.

Equilibration buffer: 20 mM Tris-HCl, 5 mM $CaCl_2$, 0.25 M NaCl, 9% isopropanol, pH 6.9±0.2 washing buffer: 10 mM Tris-HCl, 5 mM $CaCl_2$, pH 6.8±0.2

A Elution buffer: 10 mM Tris-HCl, 10 mM K-phosphate 0.5 mM $CaCl_2$, pH 6.8±0.2

5. Reversed Phase HPLC (RP-HPLC)

5.1 Separation Principle

The RP-HPLC material e.g. Vydac C4 (Vydac, USA) is composed of silica gel particles whose surface carries C4 alkyl chains. EPO binds to this matrix due to hydrophobic interactions and is selectively eluted with an acetonitrile gradient in dilute trifluoroacetic acid.

5.2 Procedure

The preparative HPLC is carried out at a temperature of 22±4° C. using a Merck Prepbar 100 separator (or an equivalent). The separation column (100 mm×400 mm, 3.2 l) is packed with Vydac C4 material. Before use the column is regenerated by applying several times a gradient of buffer A to 100% solvent and it is subsequently equilibrated with buffer A.

The eluate of the hydroxyapatite column is acidified to ca. pH 2.5 with trifluoroacetic acid and sterilized by filtration. Subsequently it is applied to the column at a temperature of 22±4° C. and a flow rate of 250–310 ml. The column is eluted at the same temperature and flow rate with a linear gradient from buffer A to buffer B. The elution peak is collected in fractions. The eluate is immediately neutralized by placing it in 4 volumes HPLC dilution buffer.

Fractions which have a purity of at least 99% in analytical HPLC are pooled (pool volume ca. 4–6 l). Trace impurities are separated in this chromatography and a purity of over 99% is achieved.

Buffer A: 0.1% trifluoroacetic acid in water

Buffer B: 80% acetonitrile, 0.1% trifluoroacetic acid in water

HPLC dilution buffer: 10 mM Na/K-phosphate, pH 7.5±0.2

6. DEAE-Sepharose ff Chromatography 6.1 Separation Principle

DEAE Sepharose fast flow (Pharmacia) is composed of DEAE groups which are covalently bound to the surface of Sepharose beads. EPO binds to this matrix due to ionic interactions and is eluted by increasing the ionic strength.

6.2 Procedure

The chromatography column (Amicon P90×250 or an equivalent) is filled with 100–200 ml gel per g applied EPO and regenerated with 0.5 N NaOH. Subsequently the column is firstly equilibrated with 100 mM Na/K-phosphate buffer, pH 7.5 and then with at least 12 CV equilibration buffer.

The eluate of the HPLC column is applied to the column at a temperature of 5±4° C. and a flow rate of ca. 150 ml/min. The column is washed at the same temperature and flow rate with at least 5 CV equilibration buffer and then with ca. 10 CV washing buffer. subsequently it is again washed with ca. 10 CV equilibration buffer and then eluted with ca. 7 CV elution buffer. The total protein peak is collected (ca. 2–5 l), sterilized by filtration and dispensed.

During this chromatography the solvent from the HPLC step is separated and trace impurities are removed. The purity is more than 99%.

Equilibration buffer: 10 mM Na/K-phosphate, pH 7.5±0.2

Washing buffer: 30 mM Na-acetate, pH 4.5±0.1

Elution buffer: 10 mM Na/K-phosphate, 80 mM NaCl pH 7.5±0.2

List of References

Bavister, B., J. Expcology 217 (1981) 45–51
EP-A 0 248 656
EP-A 0 267 678
EP-A 0 307 247
EP-A 0 343 635
EP-A 0 481 791
EP-A 0 513 738
EP-B 0 148 605
EP-B 0 205 564
EP-B 0 209 539
EP-B 0 411 678
Huang, S. L., PNAS, USA 81 (1984) 2708–2712
Kawamoto, T. et al., Analytical Biochem. 130 (1983) 445–453
Kowar, J. und Franek, F., Methods in Enzymology 421 (1986) 277–292
Lai, P.H. et al., J. Biol. Chem. 261 (1986) 3116–3121
Nobuo, I., et al., J. Biochem. 107 (1990) 352–359
Protein Purification Methods, A practical approach, Ed. Harris, E. L. V. and Angal S., IRL Press, Oxford, England (1989) page 224
Protein Purification, Ed. Janson, J. C., Ryden, L., VCH-Verlag, Weinheim, Deutschland (1989), pages 207–226.
Sasaki, H. et al., J. Biol. Chem 262 (1987) 12059–12076
WO 86/07494
WO 88/00967
WO 91/09955
WO 93/09222

What is claimed is:

1. A process for the production of a preparation comprising a protein with erythropoietin activity, comprising the steps of expressing DNA coding for the protein in a mammalian host cell by a fermentation step of the mammalian host cell without any contact between serum and the mammalian host cell such that all DNA expression occurs in a serum free medium which is free of nonrecombinant mammalian proteins, chromatographically purifying the protein from the cell supernatant by dye affinity chromatography, chromatography on hydroxyapatite, reversed phase chromatography and anion exchange chromatography, wherein one of the chromatography steps carried out after the dye affinity chromatography is a hydrophobic chromatography, and then isolating said protein with erythropoietin activity, wherein said protein is in the form of a preparation which contains less than 100 ppm of proteins derived from the host cell, and less than 10 pg of host cell DNA per 83 $\mu$g erythropoietin and wherein the preparation is completely free of nonrecombinant mammalian proteins which are not derived from the host cell.

2. The process according to claim 1, wherein the hydrophobic chromatography is carried out on a butylated support.

3. The process according to claim 1, wherein the reversed phase chromatography is carried out on a butylated support at a neutral pH value.

4. The process according to claim 1, wherein the loading or the elution or both the loading and elution of the hydrophobic chromatography is carried out in the presence of an alcohol.

5. The process according to claim 4, wherein isopropanol is used in an amount of 25–35% (v/v) for the elution.

6. The process according to claim 4, wherein isopropanol in an amount of 10–15% (v/v) is used for the loading.

7. The process according to claim 1, wherein said protein is chromatographically purified in the absence of protease inhibitors.

8. The process according to claim 1, wherein said nonrecombinant mammalian proteins are not present during said process.

9. The process according to claim 1, wherein the mammalian host cell is kryopreserved, and subsequently expanded in serum-free medium.

* * * * *